United States Patent
Okada

[11] Patent Number: 6,093,196
[45] Date of Patent: Jul. 25, 2000

[54] BASKET TYPE GRASPING TOOL FOR SURGERY

[75] Inventor: Tsutomu Okada, Kunitachi, Japan

[73] Assignee: Olympus Optical Co., Ltd., Tokyo, Japan

[21] Appl. No.: 09/243,306

[22] Filed: Feb. 2, 1999

[30] Foreign Application Priority Data

Feb. 5, 1998 [JP] Japan .................................. 10-024432
Nov. 27, 1998 [JP] Japan .................................. 10-337035

[51] Int. Cl.$^7$ .................................................. A61B 17/22
[52] U.S. Cl. .......................................................... 606/127
[58] Field of Search .................................. 606/127, 114, 606/128

[56] References Cited

U.S. PATENT DOCUMENTS 3,008,467 11/1961 Morris .
4,865,017 9/1989 Shinozuka ............................... 606/127
5,059,199 10/1991 Okada et al. ........................... 606/127
5,330,482 7/1994 Gibbs et al. ............................ 606/127
5,496,330 3/1996 Bates et al. .
5,788,710 8/1998 Bates et al. ............................. 606/127

FOREIGN PATENT DOCUMENTS 1-75415 5/1989 Japan .
5-46426 12/1993 Japan .
6-81507 11/1994 Japan .
WO 94/18888 9/1994 WIPO .
WO 96/23446 8/1996 WIPO .

*Primary Examiner*—Jeffrey A. Smith
*Assistant Examiner*—Eduardo C. Robert
*Attorney, Agent, or Firm*—Frishauf, Holtz, Goodman, Langer & Chick, P.C.

[57] ABSTRACT

A basket type grasping tool of the present invention is equipped with a basket including a plurality of groups of elastic wires. The elastic wires in the respective elastic wire groups have a branch point at the same distance position in an intermediate position from a forward end tip to a rear end tip. Since the elastic wires in the respective elastic wire groups are expanded from the branch point in a spread-apart way, a stable basket shape is maintained, so that a stone can be positively grasped in the basket.

24 Claims, 8 Drawing Sheets

BASKET TYPE GRASPING TOOL FOR SURGERY

BACKGROUND OF THE INVENTION

The present invention relates to a basket type grasping tool for surgery and, in particular, a basket type grasping tool for surgery which is transendoscopically inserted into a body cavity of a subject to allow an object, such as a stone, etc., in the body cavity to be grasped/entrapped thereby and the object to be removed out of the body cavity.

The basket type grasping tool for surgery is disclosed in JPN UM APPLN KOKOKU PUBLICATION No. 5-46426. In general, such type of grasping tool is equipped with a basket. The basket is so formed as to define a polygonal type basket as a whole with a plurality of elastic wires connected together at their forward end side and rear end side and a plurality of bent points provided at it intermediate portion.

In this basket type grasping tool, the basket is formed with individually independent elastic wires bent in their intermediate portions. When, in use, the basket was inserted into a narrower body cavity of a subject, it sometimes collapsed at an otherwise expanded region and it reduced a space in which an object was entrapped.

On the other hand, a basket of a basket type grasping tool as disclosed in U.S. Pat. No. 5,496,330 and PCT WO 94/18,888 comprises a plurality of wires (each comprised of a plurality of filaments) spirally configured with a space defined between adjacent wires.

In the basket of the U.S. Pat. No. 5,496,330 and PCT WO 94/18,888, these filaments in the respective wire are spirally formed in a uniform pattern and a resultant basket configuration becomes unstable and is hard to maintain in a narrow surrounding wall of a body cavity. And the basket is liable to be deformed in an irregular pattern with its filaments in the respective group providing a greater space than a normal. Further, since the respective space between the adjacent filaments are uniform in a portion from a rear end side toward the forward end of the basket, it is relatively large and, due to the above-mentioned drawback, a stone once being caught was sometimes dropped out of the space of the basket. For the same reason as set out above, when the rear end portion of the basket was retracted back into a sheath to cause the basket to be contracted with the stone grasped, it sometimes readily dropped out of the space of the basket. When, in particular, a small stone is to be caught or entrapped, it readily falls out of the basket.

BRIEF SUMMARY OF THE INVENTION

It is accordingly the object of the present invention to provide a basket type grasping tool which can readily catch an object in its basket even in a narrow body cavity of a subject and be less likely to drop out of the basket.

The object of the present invention is achieved by a basket type grasping tool. That is, in a basket type grasping tool for surgery which has an expandable and contractable basket provided on a distal end of an operation line insertable into a sheath to allow the operation line to be moved back and forth and capable of, when being exposed from the distal end of the sheath, being expanded in a spread-apart way and, when being retracted back into the sheath, being contracted to allow an object which is entrapped in the spread-apart basket to be grasped, the basket has a plurality of groups of elastic wires, each group having a plurality of elastic wires with a branch point provided in an intermediate section from a forward end tip to a rear end tip, and the elastic wires of the respective elastic wire groups are expanded in a spread-apart way with a space defined therebetween.

Further, according to the present invention, the elastic wires in the respective elastic wire groups are so branched at the branch point as to be spread apart from each other at a forward end section from the branch point.

Further, according to the present invention, the branched elastic wires in the elastic wire groups have bent points in the intermediate section from the forward end tip toward a rear end tip.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION (First Embodiment)

Figure 1:
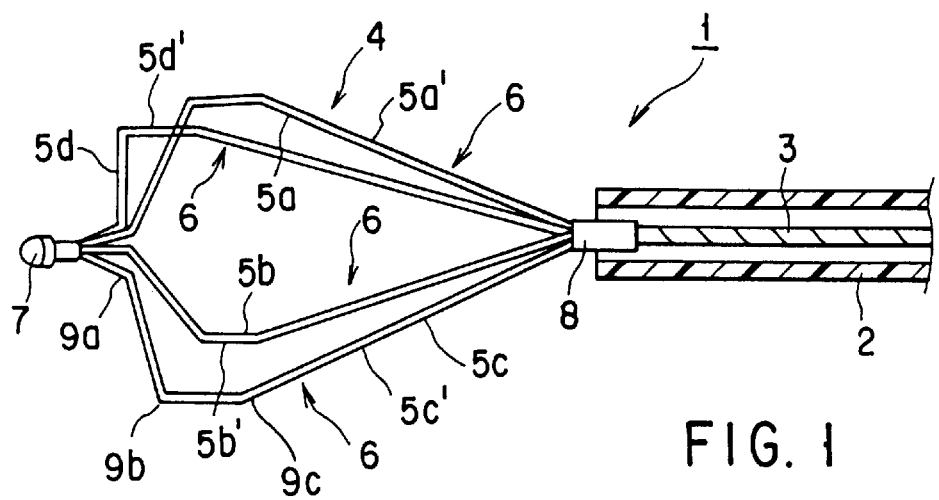
FIG. 1 is a perspective view showing a basket, and its neighborhood, of a basket type grasping tool according to a first embodiment of the present invention.

A basket type grasping tool according to a first embodiment will be described below with reference to FIGS. 1 to 5. The basket type grasping tool 1 comprises, as shown in FIG. 1, a flexible sheath 2 made of a resin, etc., insertable into a forceps channel (treating tool channel) of an endoscope, not shown, an operation line (wire) 3 adapted to be inserted into the flexible sheath 2 in a way to be movable back and forth, and a grasping basket 4 provided at a distal end of the operation line.

The basket 4 is formed in an order of FIGS. 1, 2, 3 and 4. First, the basket 4 in a state shown in FIG. 1 has a plural-wire group unit, such as a four-wire group unit, including a plurality of groups of elastic wires 5, 6, for example, 4 groups of elastic wires 5, 6, arranged mutually close to each other in a parallel way. Here, the four wire groups 6 comprise elastic wires 5a, 5a' (wire group 6), 5b, 5b' (wire group 6), 5c, 5c' (wire group 6) and 5d, 5d' (wire group 6). These four groups of elastic wires 6 have their forward end portions connected together at a forward end tip 7 and their rear end portions connected together at a rear end tip 8 of the basket. Further, the rear end portions of these wire groups are joined to the forward end portion of the operation line 3 to provide an integral unit at the rear end tip 8 side.

Figure 2:
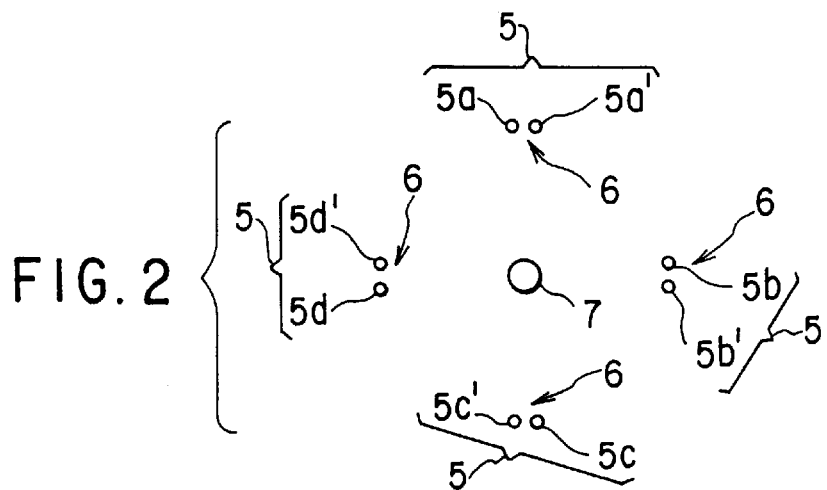
FIG. 2 is a cross-sectional view showing the basket of the basket type grasping tool according to a first embodiment of the present invention.

As shown in FIG. 2, the pairs of elastic-wires 5 in the wire groups 6 are arranged in a close-space interval such that the interval between the paired elastic wires 5 is made narrower than that between the adjacent wire groups.

An intermediate portion each of the elastic wires 5 in the wire groups 6 have folds in a direction from the forward end side toward the base end side to provide three bent points 9a to 9c at proper intervals. The bent points 9a correspond to points at which the elastic wires 5 are bent inwardly; the bent points 9b, points at which the elastic wires 5 are bent outwardly; and the bent points, points at which the elastic wires 5 are bent inwardly.

The respective bent portions 9a, . . . , 9c are formed in those corresponding equidistant positions at the individual elastic wires 5 in the wire group 6 with respect to a direction of a center axis of the basket 4. Further, the three bent portion 9a, . . . , 9c in one wire group 6 are arranged in a line-symmetrical relation to those in the opposite wire group 6. That is, these bent portions 9a, . . . , 9c occupy the same mutual corresponding positions at an intermediate portion between the forward tip end and the rear end tip of the respective wire group. That is, the respective wire groups 6 are arranged such that their respective three bent points 9a, . . . , 9c define a line symmetry with respect to a center axis of the basket 4 and, also, a three-dimensional line symmetry. This arrangement provides an expanded basket configuration. The respective wire groups 6 are located in their radial planes about the center axis of the basket 4 and these bent points 9a, . . . , 9c are bent in their radial planes and in their plane directions. By such an arrangement, the basket 4 is contractable toward, and expandable away from, the axis of the operation line 3, that is, the center axis of the basket 4. In a free state, the basket itself expands, as shown in FIG. 1, under its own elastic recovery force from the elastic wire group unit.

Here, although the bent points 9a, . . . , 9c are so formed as to be clearly bent at these points as already set out above, those paired wires 5 of the respective wire groups 6 may be so formed in a gently curved way without being locally bent as to have one of the paired wires 5 to be parallel to the other wire.

A connector, not shown, is provided at a proximal end of the flexible sheath 2 to allow a liquid or a solution to be sent through the connector. An operation section, not shown, is provided at the base end of the connector and equipped with an operation means for moving the operation line 3 back and forth. By the operation means, the operation line 3 is advanced to allow the basket 4 which is attached to the distal end of the operation line 3 to be projected or exposed from the distal end of the flexible sheath 2 and expand the basket 4 and the operation line 3 is pulled back to allow the basket 4 to be retracted back into the distal end portion of the flexible sheath and contracted.

In the respective wire groups 6 of the basket 4 in the embodiment shown in FIG. 1, the respective mutually adjacent respective paired wires 5 are joined together, at least one place between the forward end tip 7 and the rear end tip 8, by a fixing means, such as brazing, soldering and bonding agent. Here, in its practical form, the these adjacent respective paired wires 5 are joined at the bent point 9c as shown in FIG. 3.

Figure 3:
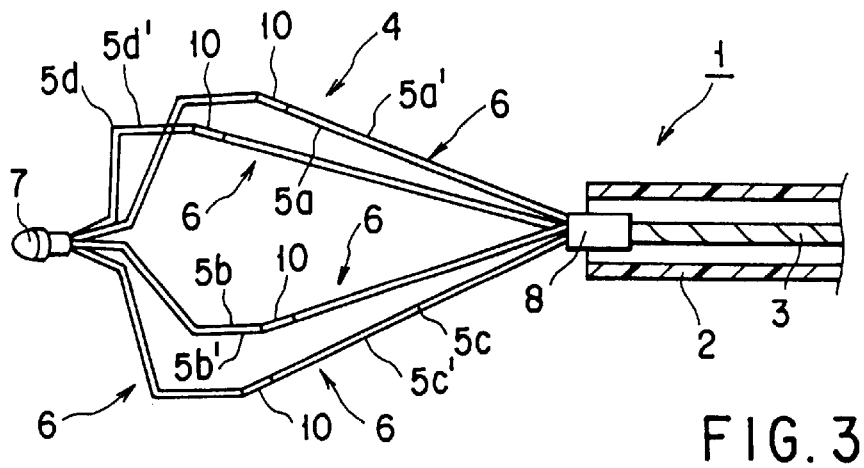
FIG. 3 is a perspective view showing a basket, and its neighborhood, of the basket type grasping tool according to a first embodiment of the present invention.
Figure 4:
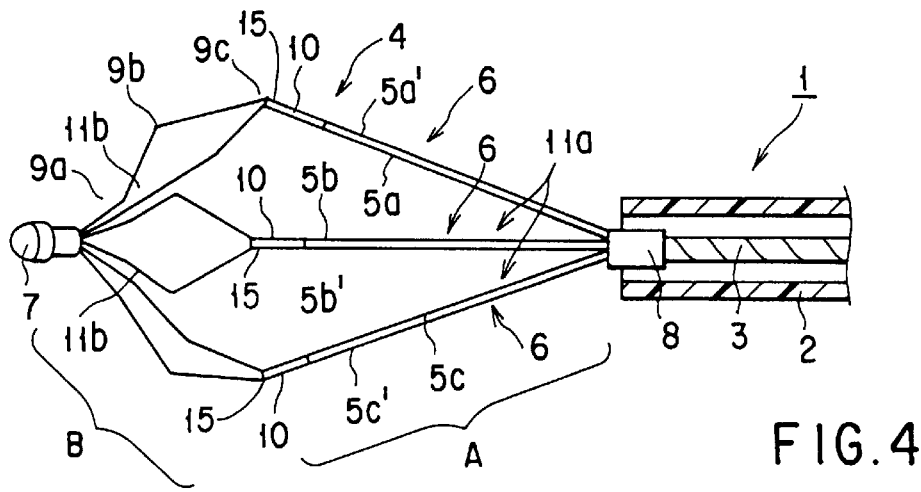
FIG. 4 is a perspective view showing a basket, and its neighborhood, of the basket type grasping tool according to a first embodiment of the present invention.

Then the basket 4 of the form as shown in FIG. 3 is further formed so as to obtain a form as shown in FIG. 4. That is, the two elastic wires 5 in the respective paired wire groups 6 extend in a substantially parallel, mutually close way in a section A from the rear end tip 8 to the bent point 9c at the rearmost side and are so branched as to be spread away from each other in a section B from the bent point 9c toward the forward end tip 7 side. In other words, a branch point 15 is provided to obtain a gradually mutually spaced-apart relation from the bent point 9c toward the forward end tip side.

Figure 5:
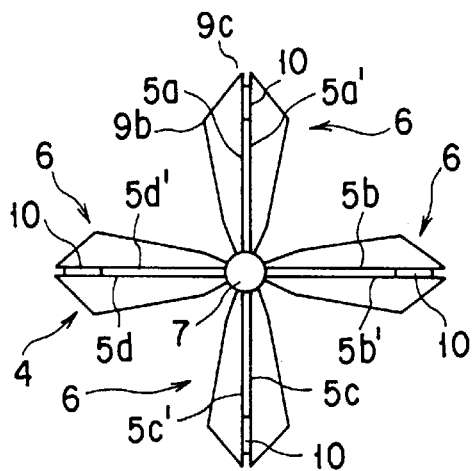
FIG. 5 is a front view showing a basket of the basket type grasping tool according to a first embodiment of the present invention.

Then the two elastic wires 5 in the respective paired wire groups 6 are so formed as to converge from the bent point 9b to the forward end tip 7. The two elastic wires 5 in the respective paired wire group 6 extend in the mutually parallel, mutually close way in the section A and is so branched as to be spread away from each other in the section B. In the state shown in FIG. 4, the resultant basket, being viewed from a forward end side, looks like a dart's flight as shown in FIG. 5.

The order of creating the basket is not restricted to the above-mentioned order only.

Then this basket type grasping tool 1 will be explained below as being applied to the removal of a gallstone. In use, the basket 4 is set in a state in which it is retracted in the sheath 2. The basket type grasping tool 1 in this state is inserted via a channel of a side-viewing type endoscope with a forceps raising base into a body cavity of a subject and the distal end of the flexible sheath 2 is projected, for example, into the duodenal papillae and then into the biliary tract.

Then the operation line 3 is advanced by the operation section to project the basket 4 from the flexible sheath 2. The respective wire groups 6 of the basket 4 are expanded under an elastic force of the elastic wires 5 to provide a basket configuration as shown in FIGS. 4 and 5. A gallstone is entrapped in the expanded basket 4 and, in this state, the operation wire 3 is pulled back at the operation section to contract the basket 4. By doing so, the stone is grasped within the contracted basket. And the basket type grasping tool 1, together with the endoscope, is withdrawn out of the sheath and the stone is removed.

Since the respective wire groups 6 are each comprised of plural elastic wires 5, the expanded basket 4 is less likely to collapse in a narrower tract under a surrounding internal wall and maintains a predetermined configuration, so that a foreign matter, such as stones, can be readily entrapped within the basket 4. Further, as shown in FIG. 4, the basket 4 is spread apart each other in the section B from the bents point 9c toward the forward end tip side and then converges to the forward end tip from the bent points 9b. A maximum width of each space 11a defined between the paired elastic wires 5 in the rearward section A of the basket 4 is made narrower than that of each space 11b between the paired elastic wires 5 in the forward section B. As a result, a closer distance is defined between the respective elastic wire 5 and the adjacent elastic wire 5 at the forward section B of the basket 4 so that any foreign matter, such as gallstones, is hard to fall from between these elastic wires 5. Therefore, the stone once entrapped from the rearward spaces 11a can be positively caught by the forward section B of the basket and is not readily fall out of the basket. Since the elastic wires of the respective wire groups 6 are so configured as to be partly joined by the fixing agent 10 in the intermediate portions, when the basket 4 is compressed under a surrounding internal wall of the body cavity, the elastic wires in the respective wire groups are prevented from being individually separated apart from each other in a irregular pattern, etc., and being unbundled. And the basket 4 never collapses into an irregular shape or pattern.

Figure 6:
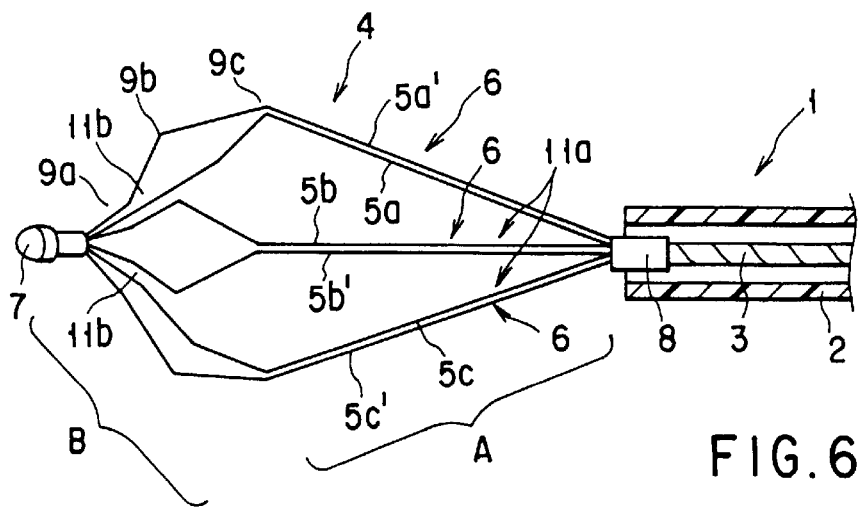
FIG. 6 is a perspective view showing a variant of the basket type grasping tool.

Even the basket 4 of a configuration as shown in FIG. 1 can be used as it is and, even in this case, the basket is stable in configuration, retains its proper pattern and can positively grasp the object without irregularly collapsing in a narrower body cavity or tract. Further, the basket 4 of the configuration as shown in FIG. 3 can be used as it is and, in this case, the respective elastic wires 5 in the respective wire groups 6 are not unbundled and never collapse into an irregular configuration. Although, in this form, the elastic wires in the respective wire groups 6 of the basket 4 are connected together near a branch section 15, a form as shown in FIG. 6 can be used where two elastic wires 5 in respective wire groups 6 are not bundled.

Figure 7:
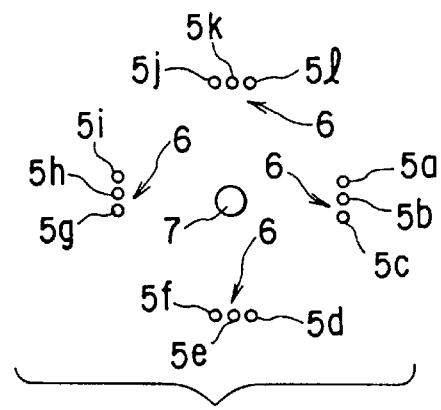
FIG. 7 is a cross-sectional view showing the variant of the basket of the basket type grasping tool.

When the type of form as shown in FIG. 1 is used as it is, a practical form as shown in FIG. 7 may be used in which three elastic wires in each wire group are used instead of two elastic wires. The form as shown in FIG. 7 is similar to that as shown in FIG. 1 except at this point.

(Second Embodiment)

Figure 8:
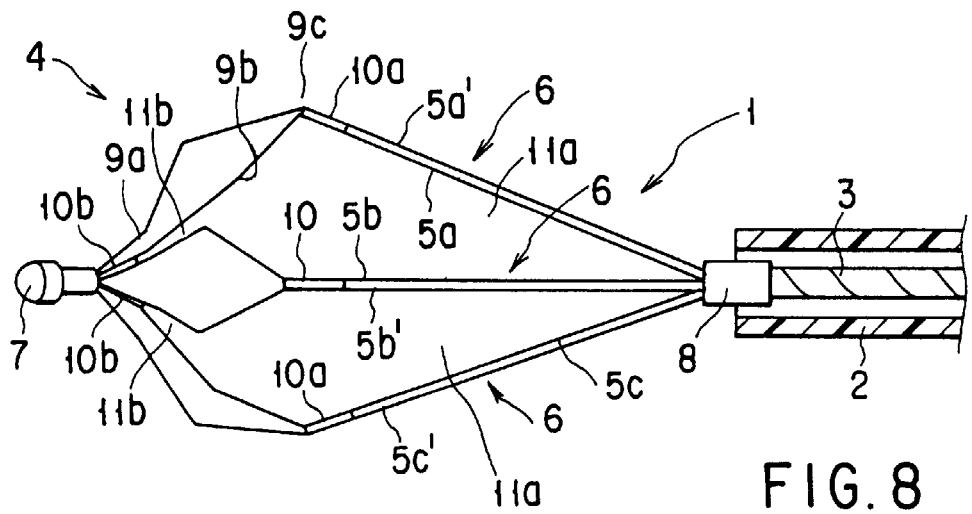
FIG. 8 is a perspective view showing a basket, and its neighborhood, of a second embodiment of the present invention.
Figure 9:
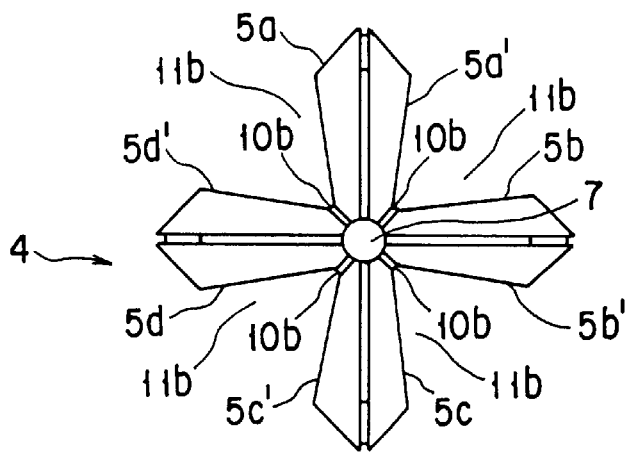
FIG. 9 is a front view of the basket type grasping tool of the second embodiment.

A second embodiment of the present invention will be explained below with reference to FIGS. 8 and 9. This embodiment is similar to the first embodiment except at the following points. In a basket of this embodiment, one branched elastic wire of one wire group 6 is arranged close to a corresponding branched wire of another adjacent wire group 6 in an intermediate section from a forwardmost bent point 9a toward a forward end tip to provide a new wire group 6 (5a' and 5b, 5b' and 5c, 5c' and 5a). The elastic wires of each new wire group are joined together by a fixing agent 10b at a position near the forward end tip of the basket.

In this way, the elastic wires 5 of the new wire groups are spread apart from each other to provide a new branched configuration. The resultant basket has those new elastic wire groups made narrower in the forward space 11b than in the rearward space 11a. As a result, the stone once being entrapped is less likely to fall out of the basket. Further, the mutually adjacent branched elastic wires (5a' and 5b, etc.) are hard to be separated from each other and it is possible to positively prevent them from being widened.

(Third Embodiment)

Figure 10:
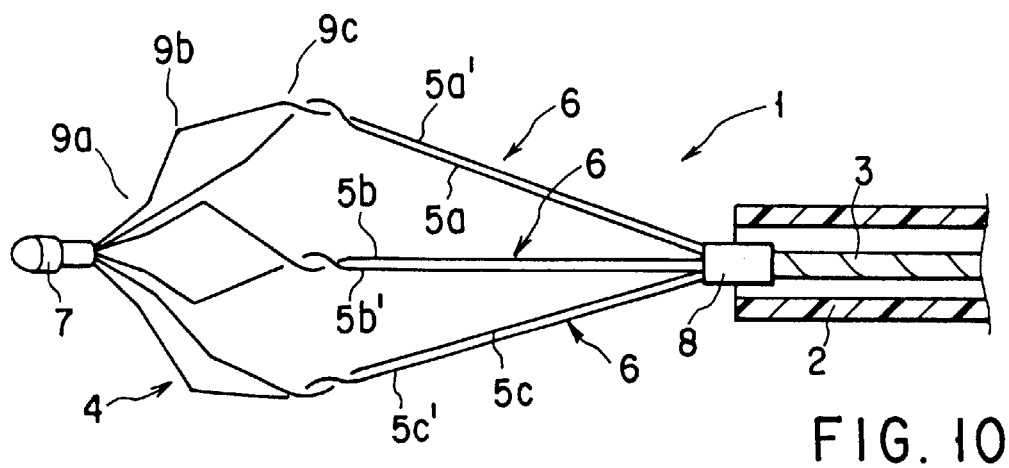
FIG. 10 is a perspective view showing a basket, and its neighborhood, showing a basket type grasping tool according to a third embodiment of the present invention.

A third embodiment of the present invention will be explained below with reference to FIG. 10. In this embodiment, paired elastic wires 5 in those wire groups constituting a basket 4 are so formed as to have the paired wires twisted or twined near a rearmost end side bent point 9c to provide a connected area at which the elastic wires are spread apart from each other. By doing so, plural wires 5 of each wire group can be fixedly joined together without the need to use the fixing agent.

(Fourth Embodiment)

Figure 11:
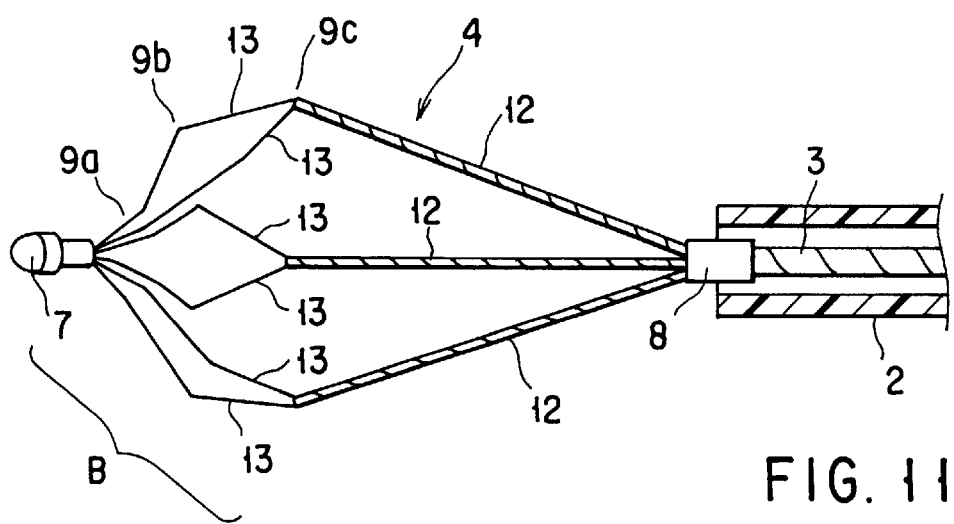
FIG. 11 is a perspective view showing a basket, or its neighborhood, showing a basket type grasping tool according to a fourth embodiment of the present invention.

A fourth embodiment of the invention will be explained below with reference to FIG. 11. In this embodiment, respective elastic wire groups each comprise a plural-wire strand 12. The elastic wires 13 of the respective wire groups are branched and expanded near a rearmost-side bent point 9c. And at a forward-side section B of a resultant basket the elastic wires are expanded at the branched point.

By doing so, it is possible for the basket to retain a predetermined shape by those spatially spread-apart elastic wires 13 in the forward-side section B.

(Fifth Embodiment)

Figure 12:
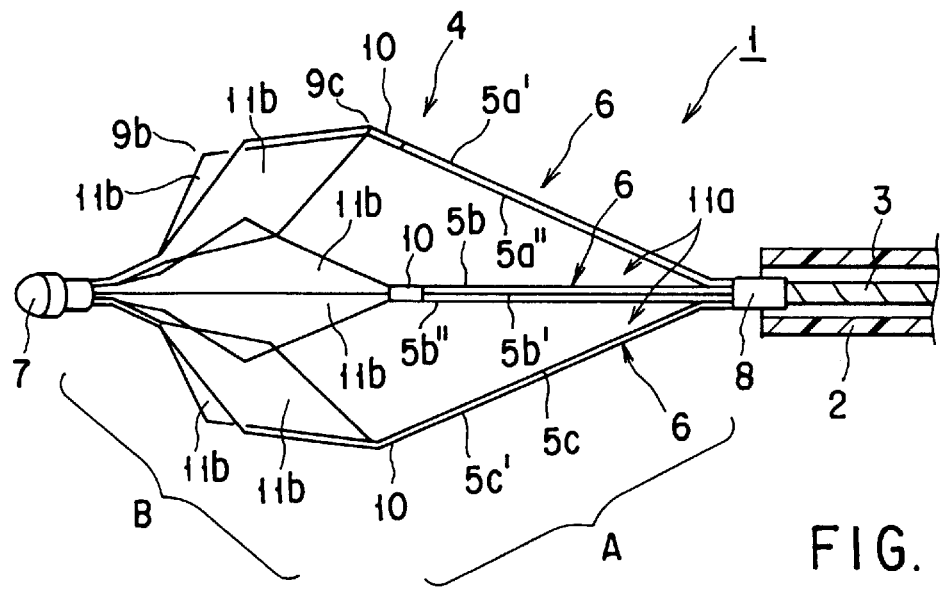
FIG. 12 is a perspective view showing a basket, and its neighborhood, showing a basket type grasping tool according to a fifth embodiment of the present invention.
Figure 13:
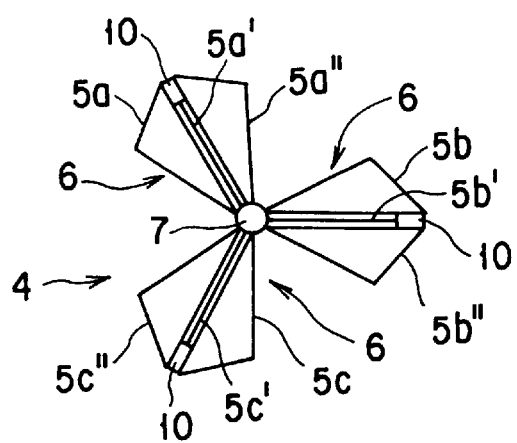
FIG. 13 is a front view showing the basket type grasping tool according to the fifth embodiment of the present invention.

A fifth embodiment of the present invention will be explained below with reference to FIGS. 12 and 13. According to this embodiment, a basket 4 is formed as will be set out below. That is, wire groups 6 are each comprised of three elastic wires 5. These three elastic wires 5 in the respective wire groups extend in a substantially parallel, mutually close way, as in the case of FIG. 3, in a section A from a rear end to a bent point 9c at a rearmost end side. In a section B from the bent point 9c toward a forward tip end side, as shown in FIG. 13, these respective three elastic wires are so expanded that two (5a, 5a", 5b, 5b" and 5c, 5c"), left and right, of the three elastic wires in the respective wire groups are spread apart each other with a remaining elastic wire as a center elastic wire (5a', 5b', 5c'), that is, so expanded as to provide a branched configuration in a direction from the bent point 9c toward the forward end tip. The two elastic wires, left and right, gradually converge toward the center elastic wire and hence toward the forward end tip side from a second bent point 9b.

In the neighborhood of the bent point 9c, the three elastic wires in the respective wire groups are fixedly joined together by brazing, soldering and fixing agent 10 such as a bonding agent. That basket structure, as being viewed from the forward side, looks like a dart flight as shown in FIG. 13.

According to this embodiment, those spaces 11a between the adjacent elastic wire groups 6 at a rearward section A of the basket 4 are greater than those spaces 11b of the adjacent wires 5 at a forward section B of the basket, so that it is easier to entrap a stone at the spaces 11a. Further, since in the forward section B the elastic wires 5 are expanded in a spread-apart relation, the basket 4 retains a stable configuration. As a result, a caught stone or stones do not fall out of the spaces 11b between the elastic wires 5 and, once being entrapped in the basket, are hard to drop during a removal of the stone. And it is also effective to entrap or catch a small stone or stones.

(Sixth Embodiment)

Figure 14:
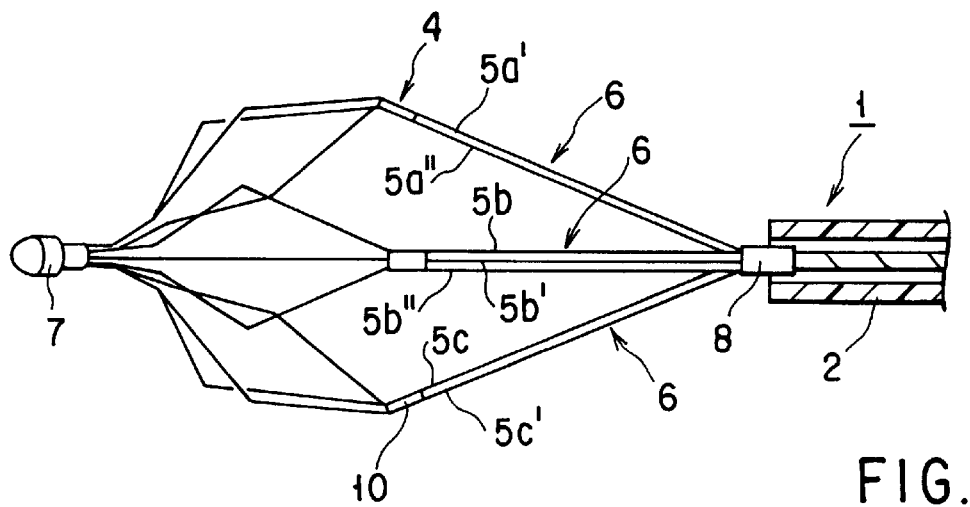
FIG. 14 is a perspective view showing a basket, and its neighborhood, showing a basket type grasping tool according to a sixth embodiment of the present embodiment.
Figure 15:
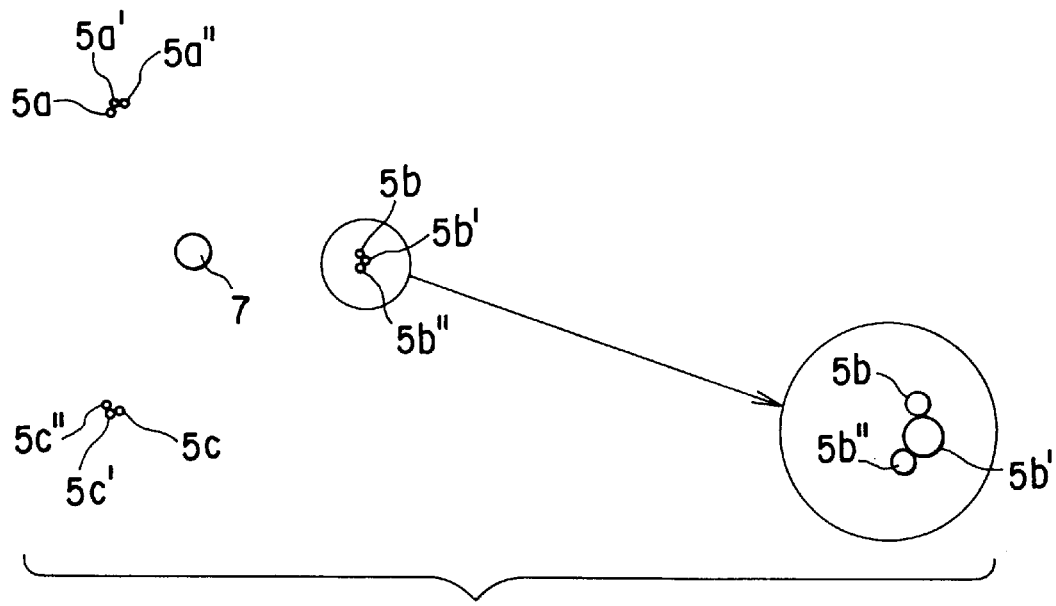
FIG. 15 is a cross-sectional view showing a basket, and its neighborhood, showing the basket type grasping tool according to the sixth embodiment of the present invention.
Figure 16:
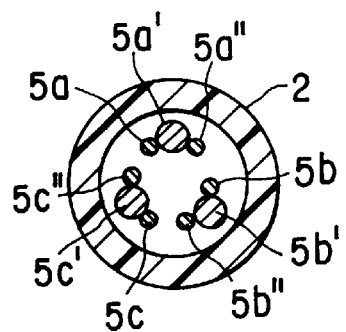
FIG. 16 is a cross-sectional view showing a sheath into which the basket of the basket type grasping tool according to the sixth embodiment of the present invention is retracted back.

A sixth embodiment of the present invention will be explained below with reference to FIGS. 14 to 16. This embodiment is different from the fifth embodiment in the following point. That is, three elastic wires 5 of a respective elastic wire group 6 in a basket of the sixth embodiment are such that, out of these three elastic wires, a center elastic wire (5a', 5b', 5c') are thicker in diameter than the remaining two elastic wires, left and right. Except at this point, the sixth embodiment is the same as the fifth embodiment.

According to the sixth embodiment, since the center elastic wires 5a', 5b', 5c' of the elastic wire groups 6 are thicker in diameter, the basket 4 can be expanded in a stably spread-apart pattern. As shown in FIG. 16, when the basket 4 is retracted back into a sheath 2, it is readily done in a stabler, smoother and positive way.

(Seventh Embodiment)

Figure 17:
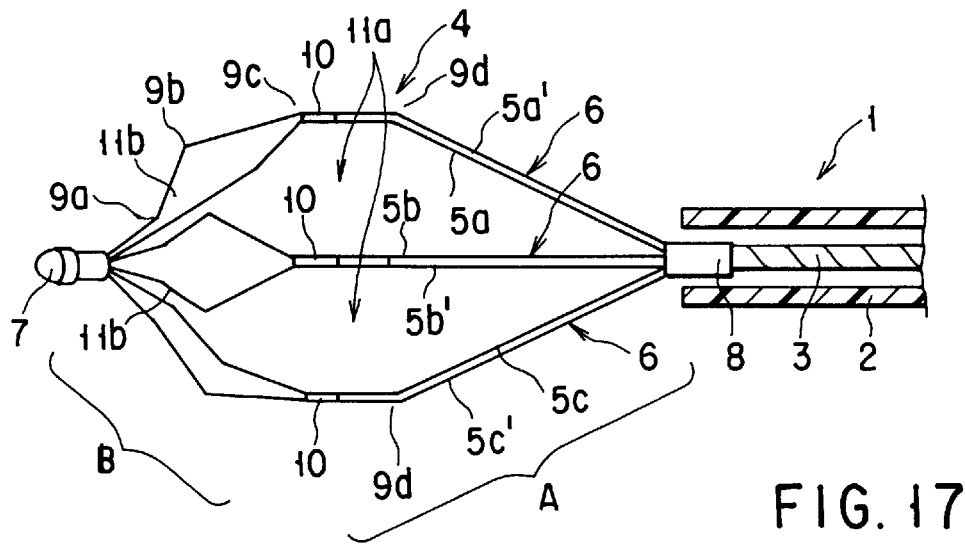
FIG. 17 is a perspective view showing a basket, and its neighborhood, showing a basket type grasping tool according to a seventh embodiment of the present invention.

A seventh embodiment of the present invention will be explained below with reference to FIGS. 17 and 18. This embodiment constitutes a variant of the sixth embodiment. This embodiment is different from the sixth embodiment with respect to a bent point 9 at a basket 4. That is, as shown in FIG. 17, a new bent point 9d is provided between a bent point 9c joined by a fixing agent 10, etc. and a rear end tip 8.

Figure 18:
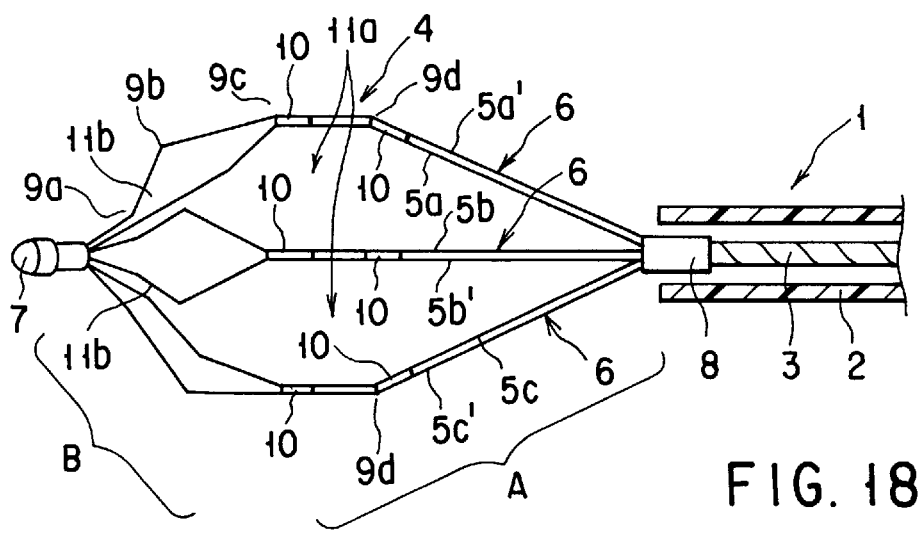
FIG. 18 is a perspective view showing a basket, and its neighborhood, showing another form of the seventh embodiment.

As shown in FIG. 18, a wire area near the bent point 9d may be joined by the fixing agent 10, etc.

According to the seventh embodiment, the new bent point 9d is provided at the rearward side of the bent point 9c and an entrapping storage space is made greater by that extent.

Although, in the above-mentioned embodiments, the basket has been explained as having three or four bent points, it may be used with less or more number of bent points. The elastic wire groups moreover may be joined together, by the fixing agent, etc., not only at the forwardmost end side bent point and rearmost end side bent point but also at an area near another bent point or at a branched position or at other proper positions.

(Eighth Embodiment)

Figure 19:
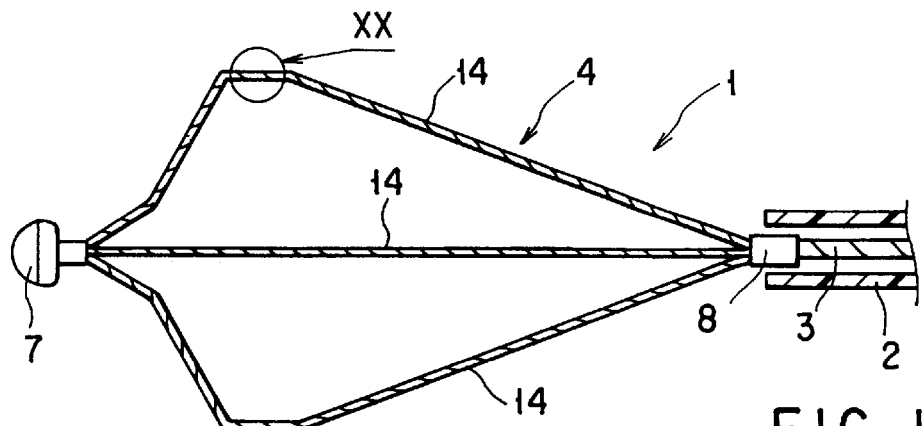
FIG. 19 is a cross-sectional view showing a basket, and its neighborhood, showing a basket type grasping tool according to an eighth embodiment of the present invention.
Figure 20:
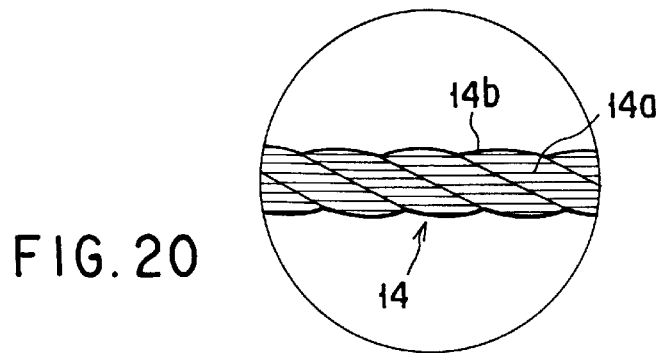
FIG. 20 is an enlarged view showing an xx section of the elastic strand cable in FIG. 19.

An eighth embodiment of the present invention will be explained below with reference to FIGS. 19 and 20. A basket type grasping tool 1 of the present invention has its basket so configured as to use the following elastic wire means. That is, the respective elastic wire means 14 constitutes a cable comprised of a plurality of strands twisted together as shown in FIG. 20 and, in this case, each strand is comprised of a plurality of wires twisted together. Further, the laying direction of the wires 14a are opposite to that of the strands 14b and, as a result, the wires 14a extend parallel to each other along an axis of the cable. By doing so, a sliding resistance of the basket 4 in the sheath 2 is alleviated to a considerable extent. This cable 14 can be used for the elastic wires 5 in the basket of the above-mentioned respective embodiment. Further, it is suitably applied to the elastic wire 12 of the fourth embodiment in particular. Needless to say, it can also be used for the elastic wire of an ordinary basket type grasping tool.

Here, although an explanation is given about the elastic wire cable constituting the basket 4, the above-mentioned operation line 3 may be similarly structured and, by doing so, the same advantage can also be obtained with respect to the operation line 3.

(Ninth Embodiment)

Figure 21:
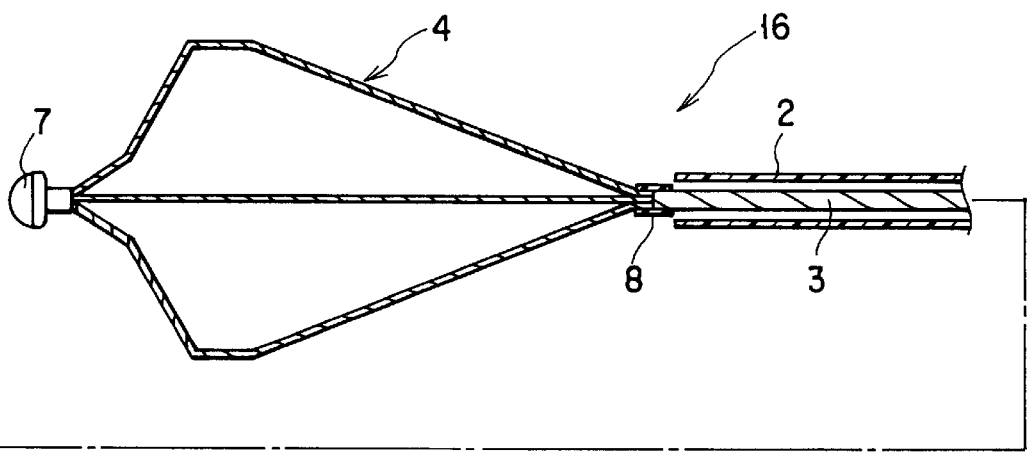
FIG. 21 is a cross-sectional view showing a basket type grasping tool according to a ninth embodiment of the present invention.
Figure 21:
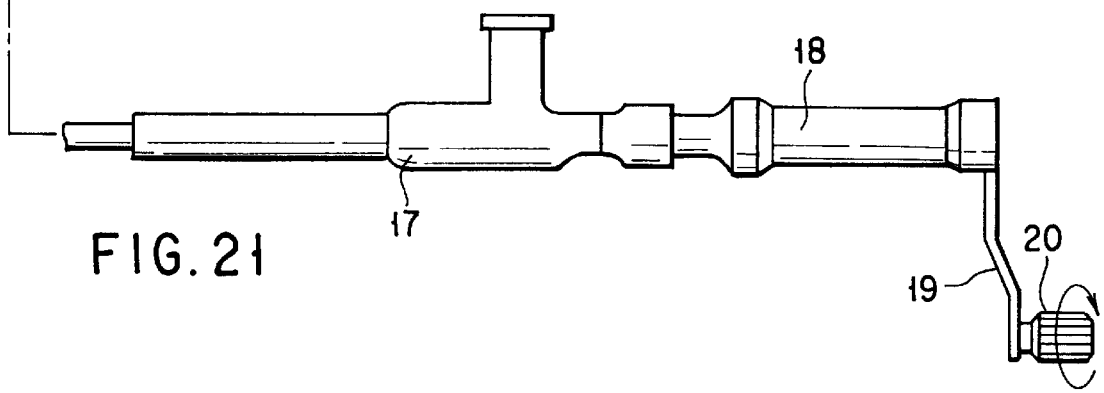
Figure 22:
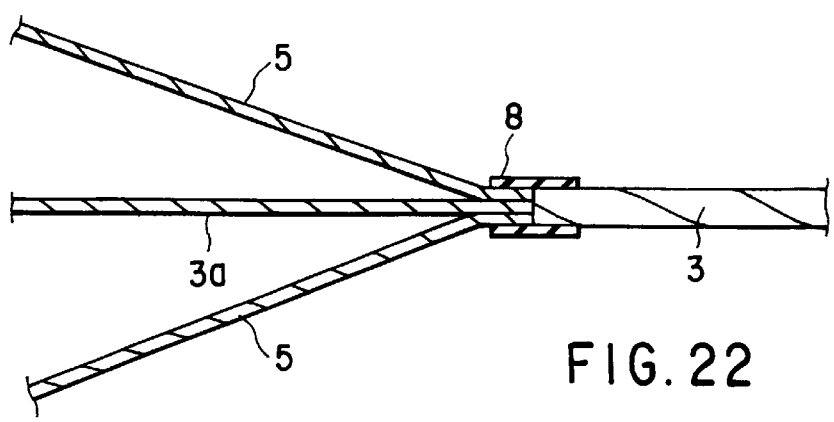
FIG. 22 is an enlarged cross-sectional view showing elastic wire sections of the basket of the basket type grasping tool of the ninth embodiment.
Figure 23A:
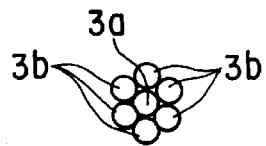
FIG. 23A is a cross-sectional view of an operation line of the basket type grasping tool of the ninth embodiment.
Figure 23B:
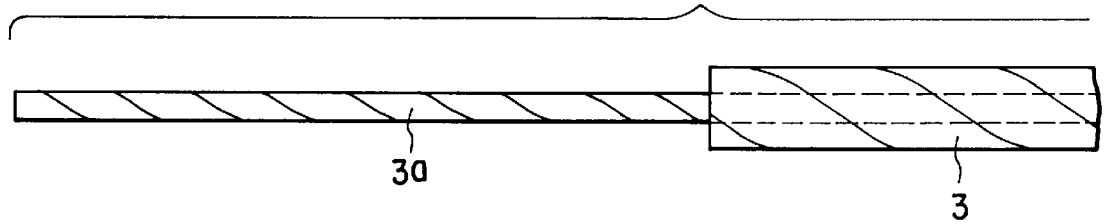
FIG. 23B is a side view showing the operation line.

A ninth embodiment of the present invention will be explained below with reference to FIGS. 21 to 23. A basket type grasping tool 16 of the present invention uses a high torque transmitting wire for the operation line 3. The operation line 3 comprises a elastic core strand 3a and a plurality of elastic side strands 3b as shown in FIG. 23. With the core strand 3a partly exposed, these side strands 3b together with the core strand are used as elastic wires. The forward end portions of these elastic strands are connected together at a forward end tip 7 and the rear end portions of the elastic strands are fixed together at the rear end tip 8 to provide a basket.

In a proximal section of the basket type grasping tool 16, a cock 17 is provided on a base end of the sheath 2 and a holding section 18 is connected to the base end of the operation line 3. An arm 19 is coupled to the holding section 18 in a manner to extend at an angle vertical to a center axis of the holding section 18. A knob 20 is attached to the free end of the arm 19 and, when the arm 19 is rotated with the knob 20 hand-gripped, the holding section 18 can be rotated. By doing so, the basket 4 can be positively rotated through the high torque transmitting operation line 3.

When the basket type grasping tool 16 is used, the basket 4 is expanded, in a spread-apart way, in the biliary tract with the knob 20 hand-grasped and the arm 19 is turned to cause the basket 4 to be rotated through the holding section 18 and operation line 3. By doing so, a stone or stones are caught in the basket 4.

In this embodiment, since the high torque transmitting wire is used for the operation line, the basket is easily be rotated and hence the stone is easily entrapped. Further, the operation line is used as part of the elastic wires in the basket, the basket 4 cannot be dropped away from the operation line. Except at this point the ninth embodiment is similar to the first embodiment.

(Tenth Embodiment)

Figure 24:
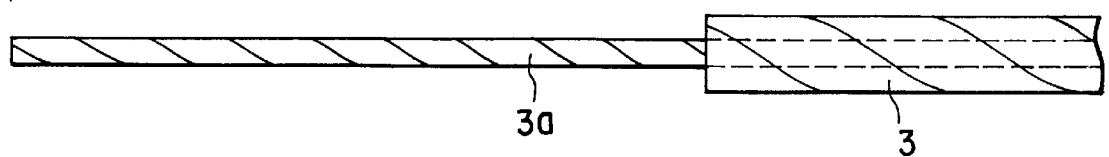
FIG. 24 is a side view showing an operation line of a basket type grasping tool according to a tenth embodiment of the present invention.

A tenth embodiment of the present invention will be explained below with respect to FIG. 24. This embodiment constitutes a variant of the ninth embodiment. In this embodiment, a core strand 3a is so made as to have its unexposed section only formed of a high torque transmitting section, so that it can be matched in this property to the elastic wires 5 of the corresponding embodiment. It is to be noted that an exposed core strand section 3a constitutes a non-torque transmitting section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A basket type grasping tool for surgery, comprising:
a sheath;
an operation line insertable into the sheath to allow the operation line to be moved back and forth; and
a basket mounted on a distal end of the operation line and capable of being expanded by being exposed from a distal end of the sheath and contracted by being retracted back into the sheath;
wherein the basket includes a plurality of groups of elastic wires, a forward end bundling portion which bundles the groups of elastic wires at distal ends thereof, and a rear end bundling portion which bundles the groups of elastic wires together with the operation line at proximal ends thereof; and
wherein each of the groups of elastic wires comprises a plurality of elastic wires which run closely in parallel to each other from the rear end bundling portion to a branching point formed at a middle portion between the forward end bundling portion and the rear end bundling portion, at which the elastic wires of each of the groups are branched and separated from one another.

2. The basket type grasping tool according to claim 1, wherein the elastic wires of the respective wire groups are branched and separated from one another at a forward section from the respective branching points thereof.

3. The basket type grasping tool according to claim 1, wherein at least plural elastic wires of the respective elastic wire groups are fixed together at at least one site in an intermediate section from the forward end bundling portion to the rear end bundling portion.

4. The basket type grasping tool according to claim 1, wherein the branched elastic wires of each elastic wire group are fixed together with the branched elastic wires of an adjacent elastic wire group at at least one site in an intermediate section of the branched elastic wires from the forward end bundling portion to the rear end bundling portion.

5. The basket type grasping tool according to claim 1, wherein the branched wires of the respective elastic wire groups are fixed together by a mutually twisted section of the elastic wires.

6. The basket type grasping tool according to claim 1, wherein the elastic wires of the respective elastic wire groups define a mutually narrower space pattern at the branched and separated portions thereof than at an other area outside the branched and separated portions thereof.

7. The basket type grasping tool according to claim 1, wherein each elastic wire group comprises two elastic wires.

8. The basket type grasping tool according to claim 1, wherein the branching point occupies a second bent point from a rearmost end side.

9. The basket type grasping tool according to claim 1, wherein the branched elastic wires of the respective elastic wire groups are fixed together at the respective branching points.

10. The basket type grasping tool according to claim 9, wherein the branched elastic wires of the respective elastic wire groups are fixed together using a fixing agent different in material from the elastic wires.

11. The basket type grasping tool according to claim 1, wherein each elastic wire group comprises three elastic wires.

12. The basket type grasping tool according to claim 11, wherein the three elastic wires of each elastic wire group are provided such that, relative to a center one of the three elastic wires, the remaining two elastic wires, left and right, are branched in an intermediate section from the forward end bundling portion to the rear end bundling portion.

13. The basket type grasping tool according to claim 11, wherein the three elastic wires of each elastic wire group are provided such that a center one of the three elastic wires is thicker than the remaining two elastic wires, left and right.

14. The basket type grasping tool according to claim 1, wherein the elastic wires each have a bent point, in an intermediate section from the forward end bundling portion to the rear end bundling portion, where the elastic wires are bent.

15. The basket type grasping tool according to claim 14, wherein the branching point of the respective elastic wire groups and the bent point of the respective elastic wires in each group are located so as to respectively occupy a same distance position in a respective back/forth direction.

16. The basket type grasping tool according to claim 14, wherein at least one branching point and at least one bent point coincide with each other.

17. The basket type grasping tool according to claims 16, wherein the at least one bent point coinciding with the at least one branching point comprises of a rearmost end side bent point.

18. The basket type grasping tool according to claim 17, wherein the coinciding at least one bent point and at least one branching point are fixed together by a fixing agent.

19. A basket type grasping tool for surgery, comprising:
a sheath;
an operation line insertable into the sheath to allow the operation line to be moved back and forth; and
a basket mounted on a distal end of the operation line and capable of being expanded by being exposed from a distal end of the sheath and contracted by being retracted back into the sheath;
wherein the basket includes a plurality of groups of elastic wires which are twisted together, a forward end bundling portion which bundles the groups of elastic wires at distal ends thereof, and a rear end bundling portion which bundles the groups of elastic wires together with the operation line at proximal ends thereof; and
wherein each of the groups of elastic wires has a branching point formed between the forward end bundling portion and rear end bundling portion, at which the elastic wires of each of the groups are branched and separated from one another.

20. The basket type grasping tool according to claim 19, wherein the three elastic wires of each elastic wire group are provided such that, relative to a center one of the three elastic wires, the remaining two elastic wires, left and right, are branched in an intermediate section from the forward end bundling portion to the rear end bundling portion.

21. The basket type grasping tool according to claim 19, wherein each elastic wire group comprises three elastic wires.

22. The basket type grasping tool according to claim 19, wherein the elastic wires of the respective wire groups are branched and separated from one another at a forward section from the respective branching points thereof.

23. The basket type grasping tool according to claims 19, wherein the elastic wires each have a bent point, in an intermediate section from the forward end bundling portion to the rear end bundling portion, where the elastic wires are bent.

24. The basket type grasping tool according to claim 23, wherein at least one branching point and at least one bent point coincide with each other.

* * * * *